(12) United States Patent
Kim et al.

(10) Patent No.: US 10,391,115 B2
(45) Date of Patent: Aug. 27, 2019

(54) ANTICANCER ADJUVANT COMPOSITION CONTAINING RIP3 EXPRESSION PROMOTER AS ACTIVE INGREDIENT, METHOD FOR SCREENING FOR ANTICANCER ADJUVANT ENHANCING SENSITIVITY OF ANTICANCER DRUG BY PROMOTING RIP3 EXPRESSION, AND METHOD FOR MONITORING SENSITIVITY OF ANTICANCER DRUG

(71) Applicant: AJOU UNIVERSITY INDUSTRY-ACADEMIC COOPERATION FOUNDATION, Seoul (KR)

(72) Inventors: You Sun Kim, Suwon-si (KR); Gi Bang Koo, Seocheon-gun (KR); Jung Ho Yun, Yeoncheon-gun (KR); Woo Jung Kim, Osan-si (KR); Yu Na Jo, Eunpyeong-gu (KR)

(73) Assignee: AJOU UNIVERSITY INDUSTRY-ACADEMIC COOPERATION FOUNDATION, Suwon-Si (KR)

(*) Notice: Subject to any disclaimer, the term of this patent is extended or adjusted under 35 U.S.C. 154(b) by 0 days.

(21) Appl. No.: 15/116,591

(22) PCT Filed: Nov. 25, 2014

(86) PCT No.: PCT/KR2014/011376
§ 371 (c)(1),
(2) Date: Aug. 4, 2016

(87) PCT Pub. No.: WO2015/119362
PCT Pub. Date: Aug. 13, 2015

(65) Prior Publication Data
US 2016/0346307 A1    Dec. 1, 2016

(30) Foreign Application Priority Data

Feb. 7, 2014 (KR) .................. 10-2014-0014242
Feb. 7, 2014 (KR) .................. 10-2014-0014243
Nov. 25, 2014 (KR) .................. 10-2014-0164963

(51) Int. Cl.
| | |
|---|---|
| A61K 31/00 | (2006.01) |
| A61K 31/706 | (2006.01) |
| A61K 45/06 | (2006.01) |
| A61K 31/337 | (2006.01) |
| A61K 31/704 | (2006.01) |
| A61K 31/7048 | (2006.01) |
| C12Q 1/6886 | (2018.01) |
| G01N 33/50 | (2006.01) |

(52) U.S. Cl.
CPC .......... *A61K 31/706* (2013.01); *A61K 31/337* (2013.01); *A61K 31/704* (2013.01); *A61K 31/7048* (2013.01); *A61K 45/06* (2013.01); *C12Q 1/6886* (2013.01); *G01N 33/5011* (2013.01); *C12Q 2600/106* (2013.01); *C12Q 2600/136* (2013.01); *C12Q 2600/154* (2013.01); *C12Q 2600/158* (2013.01); *G01N 2333/9121* (2013.01); *G01N 2333/91205* (2013.01)

(58) Field of Classification Search
None
See application file for complete search history.

(56) References Cited

U.S. PATENT DOCUMENTS

| | | |
|---|---|---|
| 7,622,106 B1 | 11/2009 | Wang et al. |
| 2002/0114809 A1 | 8/2002 | Rubinfeld et al. |
| 2002/0192282 A1 | 12/2002 | Beckert et al. |
| 2007/0274991 A1 | 11/2007 | Way et al. |

(Continued)

FOREIGN PATENT DOCUMENTS

| | | |
|---|---|---|
| CN | 102319218 A | 1/2012 |
| CN | 103417982 A | 12/2013 |

(Continued)

OTHER PUBLICATIONS

Gu Zeze et al, BMC cancer 13:1-10, 2013 (Year: 2013).*

(Continued)

*Primary Examiner* — Lei Yao
(74) *Attorney, Agent, or Firm* — Ladas & Parry LLP; Malcolm J. MacDonald

(57) ABSTRACT

The present invention relates to a pharmaceutical composition for an anticancer adjuvant containing a receptor-interacting protein kinase-3 (RIP3) protein expression inducing agent or activator as an active ingredient. The present invention also provides a method for enhancing cancer cell death, comprising administering a RIP3 protein expression inducing agent or activator in combination with an anticancer drug to cancer cells. Additionally, the present invention relates to a method for screening an anticancer adjuvant which enhances anticancer drug sensitivity by promoting RIP3 expression; and a method for monitoring anticancer drug sensitivity based on RIP3 expression. Therefore, in the case of patients lacking RIP3 expression, the use of a conventional chemotherapeutic agent after inducing RIP3 expression by pretreatment with a demethylating agent may be an effective therapeutic strategy. Also, it is expected that monitoring anticancer drug sensitivity and screening an anticancer adjuvant that enhances anticancer drug sensitivity in anticancer therapy may be an effective strategy.

4 Claims, 8 Drawing Sheets

(56) References Cited

U.S. PATENT DOCUMENTS

| | | |
|---|---|---|
| 2009/0162434 A1 | 6/2009 | Ugwoke et al. |
| 2009/0202530 A1 | 8/2009 | Sahin et al. |
| 2009/0232823 A1 | 9/2009 | Balderes et al. |
| 2010/0323034 A1 | 12/2010 | Tanigawara et al. |
| 2011/0042247 A1 | 2/2011 | Kocherlakota et al. |
| 2013/0237445 A1* | 9/2013 | Thomas ............... C12Q 1/6886 506/9 |
| 2014/0030257 A1 | 1/2014 | De La Haba-Rodriguez et al. |
| 2015/0044220 A1 | 2/2015 | Tremblay et al. |

FOREIGN PATENT DOCUMENTS

| | | |
|---|---|---|
| KR | 10-2013-0124961 A | 11/2013 |
| WO | 2008/104543 A1 | 9/2008 |
| WO | 2008/109996 A1 | 9/2008 |
| WO | 2011/028660 A1 | 3/2011 |

OTHER PUBLICATIONS

Abcam, antibody to RIP3, 2007 (Year: 2007).*
He et al, Acta Pharm Sinic 33:426-428, 2012, IDS filed Nov. 29, 2016, item AS (Year: 2012).*
Fu et al, BMC Cancer,13:1-10, 2013 (Year: 2013).*
Christman J. Oncogene 21:5483-5495, 2002 (Year: 2002).*
Supplementary European Search Report dated Jun. 14, 2017 for EP Application 14882054.1.
Japanese Office Action dated Aug. 1, 2017 with English translation for Japanese Application No. 2016-568771.
Koo, Gi-Bang,et al., "Methylation-dependent loss of RIP3 expression in cancer represses programmed necrosis in response to chemotherapeutics", Cell Research, vol. 25, No. 6, Jun. 2015, pp. 707-725.
Morgan, M. J., et al., "The serine threonine kinase RIP3: lost and found", BMB Reports, vol. 48, No. 6, Jun. 30, 2015, pp. 303-312.
Lustberg, M. B., et al., "Epigenetic Therapy in Breast Cancer", Curr. Breast Cancer Rep., vol. 3, No. 1, Mar. 2011, pp. 1-16.
Fukasawa, M, et al., "Microarray analysis of promoter methylation in lung cancers", J. Hum. Genet., vol. 51, No. 4, Apr. 1, 2006, pp. 368-374.
Tikoo, K., et al., "5-Azacytidine prevents cisplatin induced nephrotoxicity and potentiates anticancer activity of cisplatin by involving inhibition of metallothionein, pAKT and DNMT1 expression in chemical induced cancer rats", Toxicology Letters, vol. 191, 2009, pp. 158-166.
Plumb, J. A., et al., "Reversal of Drug Resistance in Human Tumor Xenografts by 2'-Deoxy-5-azacytidine-induced Demethylation of the hMLH1 Gene Promoter[1]", Cancer Research, vol. 60, No. 1, Nov. 1, 2000, pp. 6039-6044.
Tian, W., et al., "Cyclophilin D modulates cell death transition from early apoptosis to programmed necrosis induced by honokiol", International Journal of Oncology, vol. 42, No. 5, 2013, pp. 1654-1663.
New Zealand Office Action dated Feb. 8, 2017 for New Zealand Application No. 723237.
Australian Office Action dated Feb. 21, 2017 for Australian Application No. 2014382143.
Xu, J., et al., "Evidence that Tumor Necrosis Factor—Related Apoptosis-Inducing Ligand Induction by 5-Aza-2'-Deoxycytidine Sensitizes Human Breast Cancer Cells to Adriamycin", Cancer Res. vol. 67, No. 3, Feb. 1, 2007, pp. 1203-1211.
Sandhu, R., et al., "Enhancement of chemotherapeutic efficacy in hypermethylator breast cancer cells through targeted and pharmacologic inhibition of DNMT3b", Breast Cancer Res. Treat., vol. 131, 2012, pp. 385-399.
Cheetham, S., et al., "SPARC promoter hypermethylation in colorectal cancers can be reversed by 5-Aza-2'deoxycytidine to increase SPARC expression and improve therapy response", British Journal of Cancer, vol. 98, 2008, pp. 1810-1819.
Walker, S., et al., "STAT3 Inhibition by Microtubule-Targeted Drugs: Dual Molecular Effects of Chemotherapeutic Agents", Mol. Cell. Pharmacol., vol. 3, No. 1, Jan. 1, 2011, pp. 13-19.
Jezequel, P., et al., "bc-GenExMiner: an easy-to-use online platform for gene prognostic analyses in breast cancer", Breast Cancer Res. Treat., 2012, 131, pp. 765-775.
Fu, Z, et al., "The anti-tumor effect of shikonin on osteosarcoma by inducing RIP1 and RIP3 dependent necroptosis", BMC Cancer, 2013, 13:580, pp. 1-10.
He, J., et al., "Differential sensitivity of RIP3-proficient and deficient murine fibroblasts to camptothecin anticancer drugs", Acta Pharmacologica Sinica, 2012, 33, pp. 426-428.
New Zealand Office Action dated Jun. 28, 2017 for New Zealand Application No. 723237.
Fulda, S., et al., "Sensitization for death receptor- or drug-induced apoptosis by re-expression of caspase-8 through demethylation or gene transfer", Oncogene, vol. 20, 2001, pp. 5865-5877.
Australian Office Action dated Oct. 10, 2017, for Australian Application No. 2014382143.
Kazakhstan Office Action, dated Dec. 20, 2017, for Kazakhstan Application No. 2016/0792.1, with English translation.
Coupienne, et al., "RIP3 expression induces a death profile change in U2OS osteosarcoma cells after 5-ALA-PDT", Lasers in Surgery and Medicine, 2011, vol. 43, No. 7, pp. 557-564. (Abstract).
Chinese Office Action, dated May 6, 2019, corresponding to Chinese Patent Application No. 201480077473.X.

* cited by examiner

[FIG. 1]
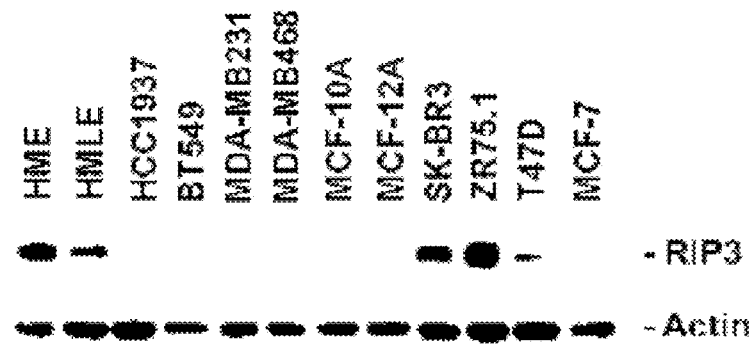
[FIG. 2]
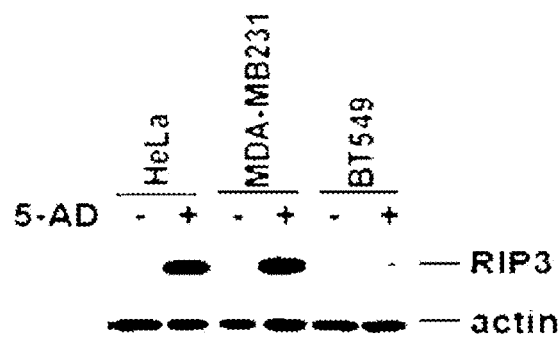
[FIG. 3]
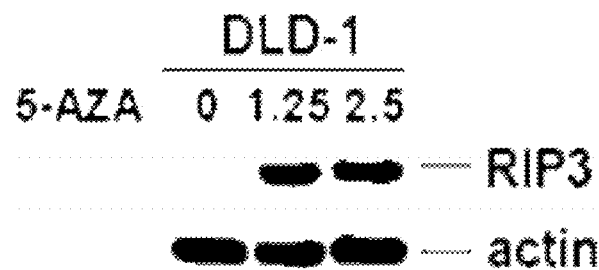

[FIG. 4]
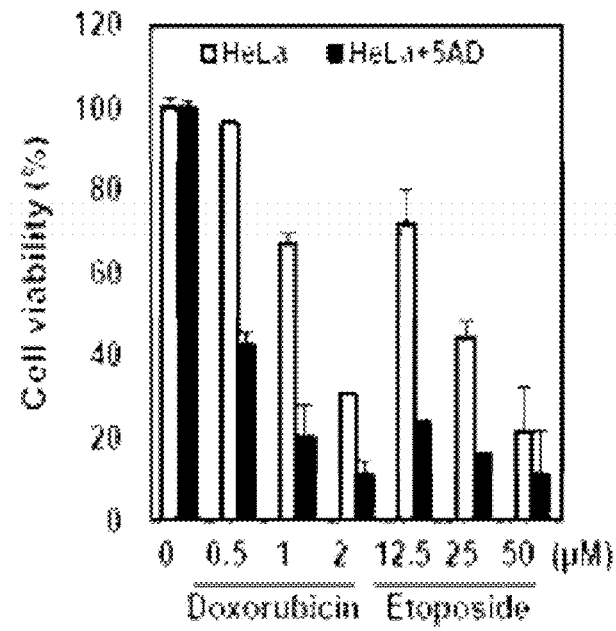
[FIG. 5]
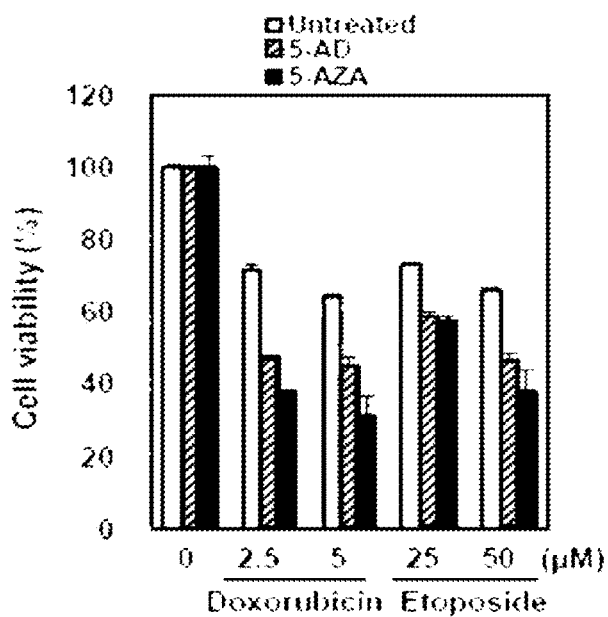

[FIG. 6]
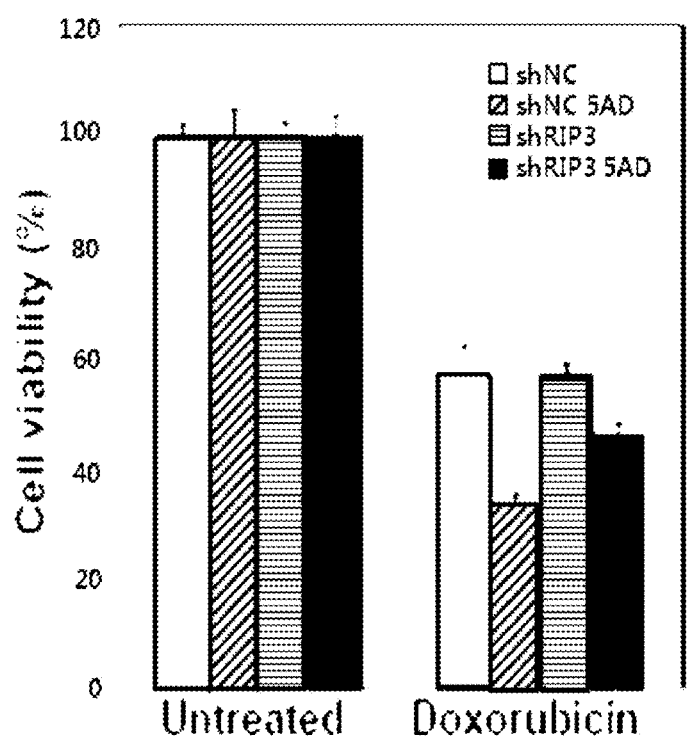

[FIG. 7]
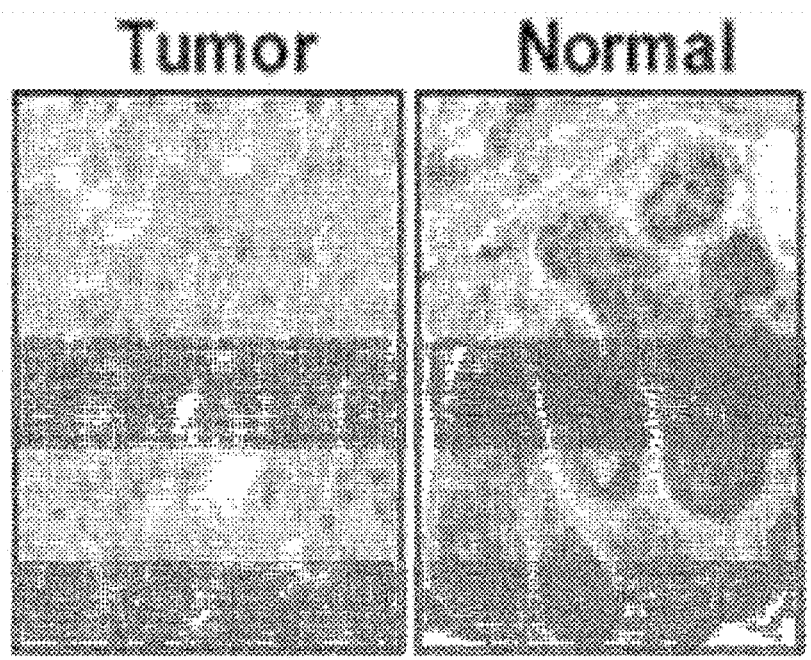
[FIG. 8]
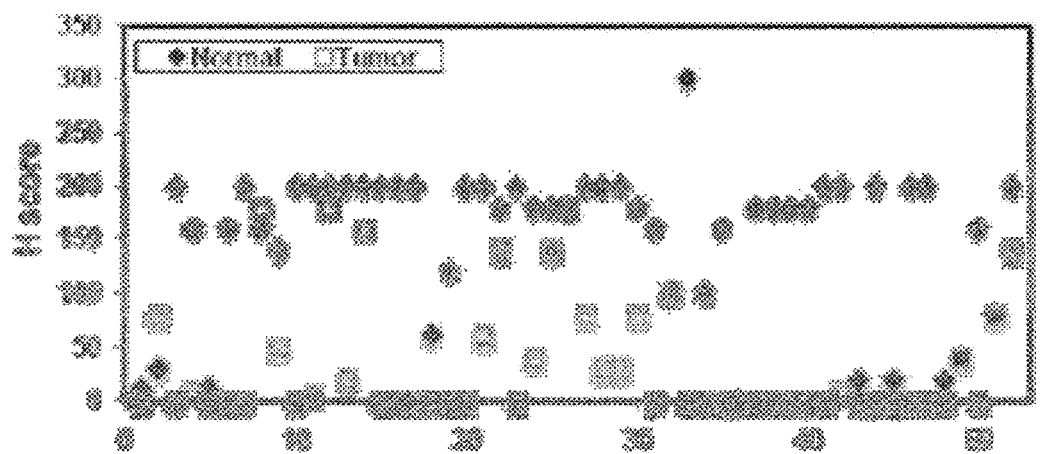

[FIG. 9]
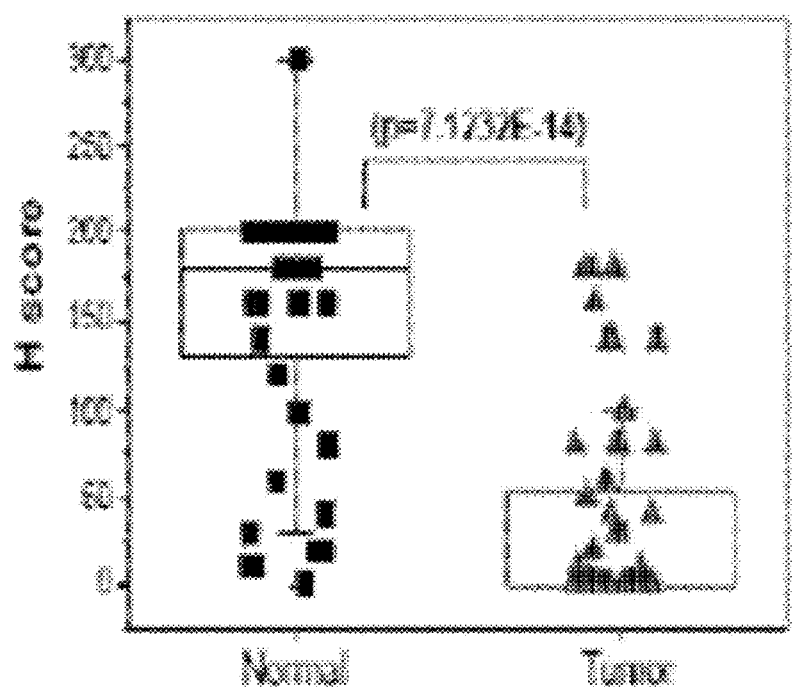

[FIG. 10]
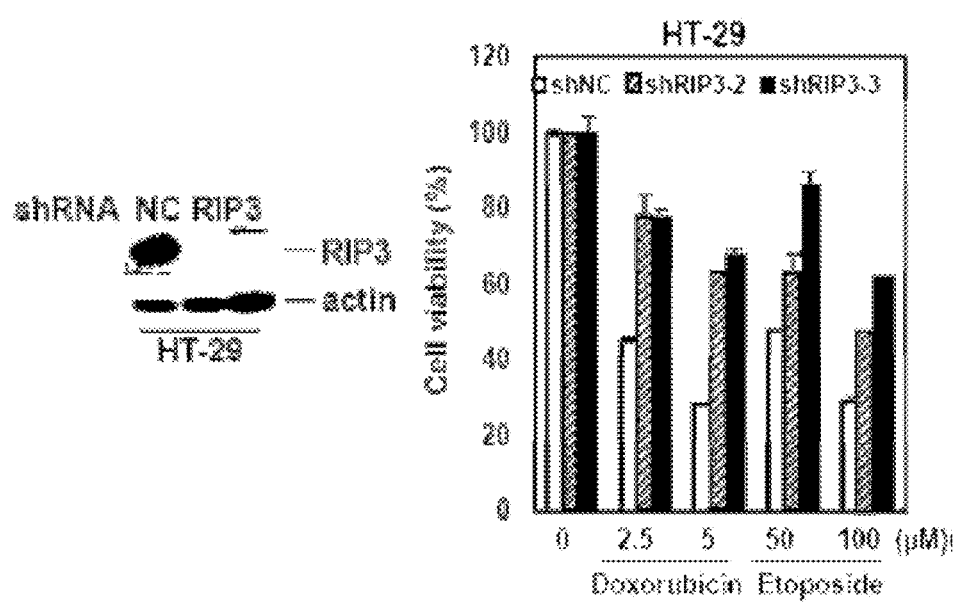

[FIG. 11]
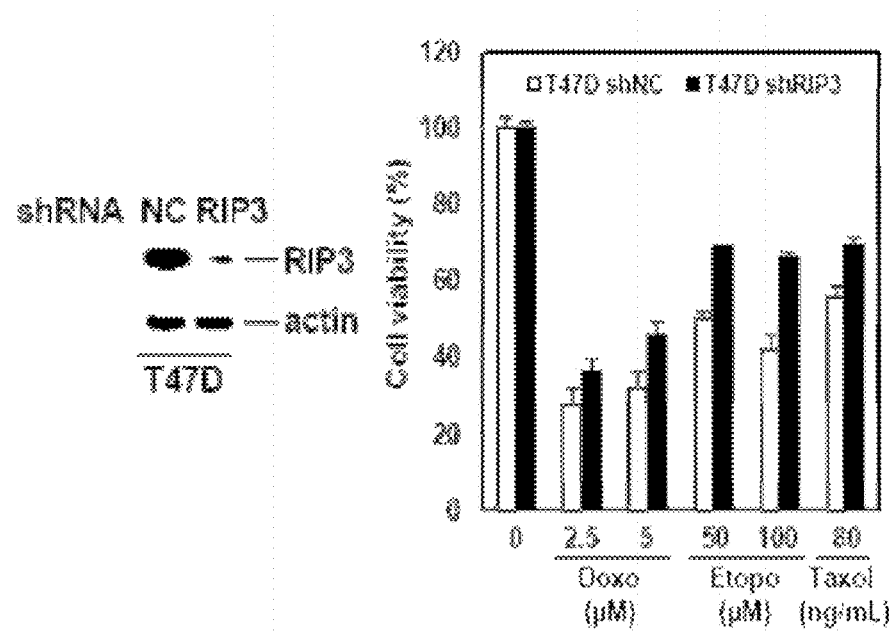

[FIG. 12]
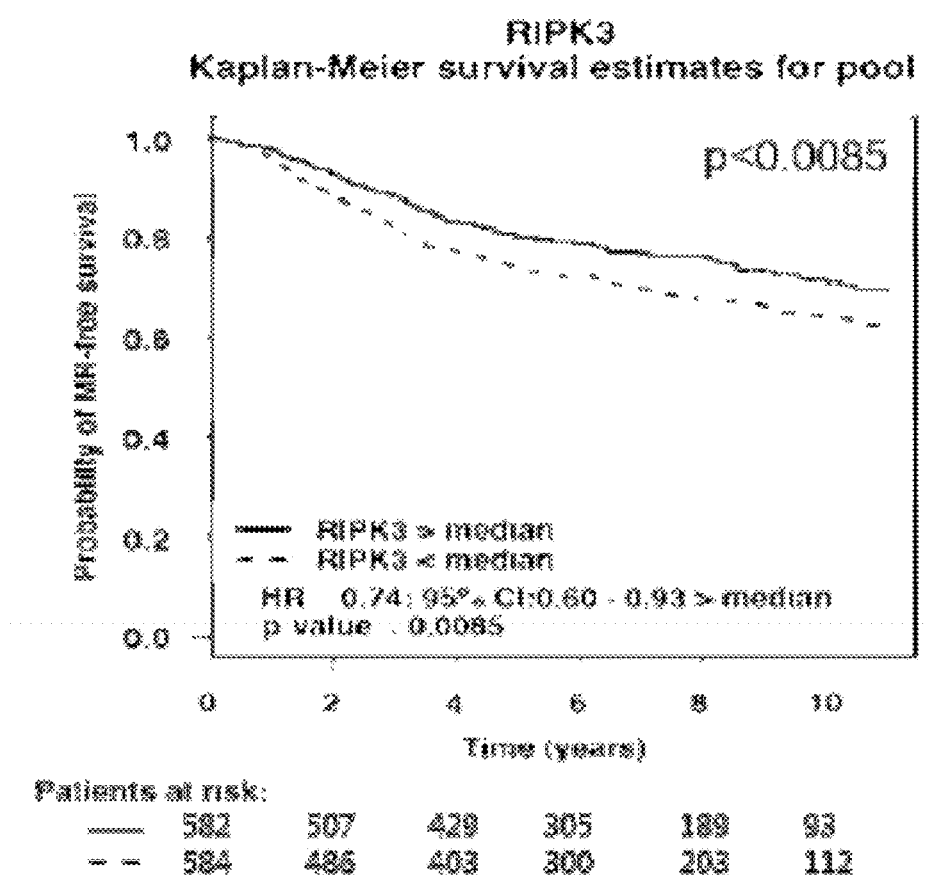

ANTICANCER ADJUVANT COMPOSITION CONTAINING RIP3 EXPRESSION PROMOTER AS ACTIVE INGREDIENT, METHOD FOR SCREENING FOR ANTICANCER ADJUVANT ENHANCING SENSITIVITY OF ANTICANCER DRUG BY PROMOTING RIP3 EXPRESSION, AND METHOD FOR MONITORING SENSITIVITY OF ANTICANCER DRUG

TECHNICAL FIELD

The present invention relates to a composition for an anticancer adjuvant containing a RIP3 expression inducing agent as an active ingredient and a method for administering the composition in combination with an anticancer drug. Moreover, the present invention relates to a method of screening an anticancer adjuvant that enhances anticancer drug sensitivity by promoting RIP3 expression and to a method of monitoring sensitivity to an anticancer drug based on RIP3 expression. In addition, the present invention provides a biomarker composition for diagnosis of anticancer drug sensitivity, which contains RIP3 gene or proteins expressed from the gene, and a method for providing information required for diagnosing prognosis of anticancer drug sensitivity.

BACKGROUND ART

Receptor-interacting protein kinase-3 (RIP3 or RIPK3) is an important protein in a cell death, and plays its role in cell death induced by death receptor or in cell death induced by other cellular stresses. It is known that these cell death signals are induced by binding to a complex with phosphorylation- or deacetylation-dependent RIP1 and mixed lineage kinase domain-like protein (MLKL) and that any protein present in mitochondria is involved in the signals. A regulated mechanism of this signaling system is induced by cell death regulatory proteins to regulate development, as well as cell death and immune responses of lymphocytes, keratinocytes and intestinal epithelial cells. In addition, regulated necrosis plays its roles in degeneration, immunity, and many etiological processes such as infectious disease and ischemic injury.

DISCLOSURE

Technical Problem

An object of the present invention is to provide a pharmaceutical composition for an anticancer adjuvant containing a receptor-interacting protein kinase-3 (RIP3) protein expression inducing agent or activator as an active ingredient, and a method for enhancing cancer cell death, which comprises administering the pharmaceutical composition for the anticancer adjuvant in combination with an anticancer drug.

Another object of the present invention is to provide a method of screening an anticancer adjuvant that enhances sensitivity to an anticancer drug by promoting RIP3 (receptor-interacting protein kinase-3) expression, and a method of monitoring anticancer drug sensitivity based on RIP3 expression.

Still another object of the present invention is to provide a biomarker composition for diagnosis of anticancer drug sensitivity, which contains RIP3 gene or a protein expressed from the gene.

Still another object of the present invention is to provide a kit for diagnosis of anticancer drug sensitivity, which comprises a primer for amplifying RIP3 gene or an antibody or aptamer that binds specifically to a protein expressed from the gene, and a kit capable of predicting and diagnosing cancer in tissue.

Yet another object of the present invention is to provide a method for providing information required for diagnosing prognosis of anticancer drug sensitivity and anticancer drug responses. The method comprises measuring expression level of RIP3 from a cancer patient sample.

Technical Solution

In order to accomplish the above objects, the present invention provides a pharmaceutical composition for an anticancer adjuvant containing a receptor-interacting protein kinase-3 (RIP3) protein expression inducing agent or activator as an active ingredient.

The present invention also provides a method for enhancing cancer cell death, which comprises administering a receptor-interacting protein kinase-3 (RIP3) protein expression inducing agent or activator in combination with an anticancer drug to cancer cells.

The present invention also provides a method for screening an anticancer adjuvant, comprising: bringing a test substance into contact with a cancer cell; measuring the expression or activity level of RIP3 (receptor-interacting protein kinase-3) protein in the cancer cell brought into contact with the test substance; and selecting a test substance that shows an increase in the expression or activity level of the RIP3 protein compared to a control sample.

The present invention also provides a method for monitoring anticancer drug sensitivity, comprising: measuring expression or activity level of RIP3 protein in a cancer cell; measuring the expression or activity level of RIP3 protein in a normal tissue cell; and determining that, if the measured expression or activity level of the RIP3 protein in the cancer cell is lower than the measured expression or activity level of the RIP3 protein in the normal tissue cell, the cancer cells have anticancer drug resistance.

The present invention also provides a method for enhancing anticancer drug sensitivity, comprising: treating a cancer cell with a RIP3 protein expression inducing agent or activator; measuring the expression or activity level of the RIP3 protein in the treated cancer cell; and determining that, if the expression or activity level of the RIP3 protein after the treatment is 50-100% higher than that of a control sample before the treatment, anticancer drug sensitivity is enhanced.

The present invention also provides a biomarker composition for diagnosis of anticancer drug sensitivity, comprising RIP3 gene or a protein expressed from the gene. The biomarker composition may also be used to predict and diagnose cancer in tissue.

The present invention also provides a kit for diagnosis of anticancer drug sensitivity, comprising a primer for amplifying RIP3 gene or an antibody or aptamer that binds specifically to a protein expressed from the gene. The use of the kit may provide information required for prediction and diagnosis of cancer in tissue.

The present invention also provides a method for providing information required for diagnosing prognosis of anticancer drug sensitivity, comprising: measuring expression level of RIP3 in a cancer patient sample; measuring the expression level of RIP3 in a normal control sample; and determining that, if the measured expression level of RIP3 protein in the cancer patient sample is lower than the measured expression level of RIP3 protein in the normal control sample, the cancer patient sample has anticancer drug resistance.

Advantageous Effects

The present invention relates to a composition for an anticancer adjuvant containing a RIP3 expression inducing agent as an active ingredient and to a method of administering the composition in combination with an anticancer drug. Currently, in 90% of triple negative (ER, PR, Her2 negative) patients who pose problems in cancer therapy, low RIP3 expression is found. A significant decrease in the expression of RIP3 in cancer tissue compared to that in normal tissue of the same patient suggests that RIP3 selectively decreases during the development and growth of tumors. Thus, in the case of patients lacking expression of RIP3, it is expected that the use of a conventional chemotherapeutic agent after the induction of RIP3 expression by pretreatment with a demethylating agent may be an effective therapeutic strategy. Moreover, the present invention relates to a method for screening an anticancer adjuvant that enhances anticancer drug sensitivity by promoting RIP3 expression and to a method of monitoring anticancer drug sensitivity based on RIP3 expression. Currently, in 90% of triple negative (ER, PR, Her2 negative) patients who pose problems in cancer therapy, low RIP3 expression is found, and it is seen that the regulation of RIP3 expression influences the anticancer drug resistance of anticancer cells. In particular, it is found that, when RIP3 expression is inhibited, cancer cells have resistance to an anticancer drug, and thus the activity of the anticancer drug is inhibited, whereas when RIP3 is expressed, the death of cancer cells increase dependently on the concentration of the anticancer drug. It is expected that analysis of expression or activity level of RIP3 may be an effective strategy for monitoring sensitivity to the anticancer drug in anticancer therapy and screening the anticancer adjuvant that enhances anticancer drug sensitivity.

DESCRIPTION OF DRAWINGS

FIG. 1 shows the results of analyzing RIP3 expression in normal breast and breast cancer cell lines.

FIG. 2 shows RIP3 expression induced by 5-aza-2'-deoxycytidine (5-AD) that is a demethylating agent.

FIG. 3 shows RIP3 expression induced by 5-azacytidine (5-AZA) that is a demethylating agent.

FIG. 4 shows the sensitization of cancer cell lines to cell death by combined treatment with a demethylating agent (5-AD) and an anticancer drug.

FIG. 5 shows the sensitization of cancer cell lines to cell death by combined treatment with a demethylating agent (5-AD and 5-AZA) and an anticancer drug.

FIG. 6 shows the inhibition of demethylating agent (5-AD)-induced sensitization of cancer cell lines to cell death by the inhibition of RIP3 expression.

FIG. 7 shows immunostaining images of RIP3 in typical normal breast tissue and breast cancer tissue.

FIGS. 8 and 9 show H-score of RIP3 immunostaining in typical normal breast tissue and breast cancer tissue.

FIG. 10 shows the viability of RIP3-silenced HT-29 cells according to various concentrations of anticancer drugs.

FIG. 11 shows the viability of RIP3-silenced T47D cells according to various concentrations of anticancer drugs.

FIG. 12 is a graph showing the results of analyzing the 10-year metastatic relapse-free survival of 1,166 breast cancer patients.

BEST MODE

The present inventors have found that RIP3-dependent cell death may influence the cytotoxicity of chemotherapeutic agents. It could be found that RIP3 expression in many cancer cell lines is inhibited and this inhibition of RIP3 expression leads not only to resistance to death receptor-induced cell death, but also to resistance to chemotherapeutic agents, particularly various standard anticancer therapeutic agents such as DNA damage drugs or taxanes. It could be found that RIP3 expression is restored by a demethylating agent 5-aza-2'-deoxycytidine (5-AD) used in the present invention and that sensitivity to the chemotherapeutic agent is increased by the demethylating agent. From such results, it can be found that, in the case of patients lacking RIP3 expression, the use of a conventional chemotherapeutic agent after the induction of RIP3 expression by pretreatment with the demethylating agent may be an effective therapeutic strategy. Based on such findings, the present invention has been completed.

In addition, the present inventors have found that the regulation of RIP3 expression influences the resistance of a cancer cell line to an anticancer drug, and particularly, have found that, when RIP3 expression is inhibited, cancer cells have resistance to the anticancer drug, and thus the activity of the anticancer drug is inhibited, whereas when RIP3 is expressed, cancer cell death is increased dependently on the concentration of the anticancer drug, thereby completing the present invention.

The present invention provides a pharmaceutical composition for an anticancer adjuvant containing a receptor-interacting protein kinase-3 (RIP3) protein expression inducing agent or activator as an active ingredient.

Particularly, the RIP3 protein expression inducing agent or activator may be selected from among compounds, peptides, peptide mimetics, aptamers, antibodies and natural substances, which bind specifically to an expression regulatory region of RIP3 gene. Particularly, the composition may induce demethylation of RIP3 protein.

Preferably, the cancer may be breast cancer, cervical cancer, liver cancer or colorectal cancer, but is not limited thereto.

Preferably, the RIP3 protein may be a protein from all eukaryotic organisms with RIP3 including mammals such as humans, cattle, goats, sheep, pigs, mice, rabbits, etc. For example, it may be human RIP3 (NCBI accession no. NP_006862.2).

As used herein, the term "peptide mimetics" refers to a peptide or non-peptide that inhibits the binding domain of RIP3 protein inducing RIP3 activity.

As used herein, the term "aptamer" refers to a single strand nucleic acid (DNA, RNA or modified nucleic acid) that has a stable 3-dimensional structure and may bind to target molecules with high affinity and specificity. Since the aptamer has unique high affinity (pM level in general) and specificity for target molecules, it is comparable with monoclonal antibodies, and in particular, its potential to be used as an alternative antibody is so high that the aptamer is often called "chemical antibody".

The "antibody" that is used in the present invention may be an antibody produced by RIP3 injection or a commercially available antibody. In addition, the antibodies include a polyclonal antibody, a monoclonal antibody and a fragment capable of binding to an epitope. The polyclonal antibody may be produced as follows. The RIPS is injected into an animal; a blood sample is taken from the animal; and then serum containing the antibody is separated from the blood. This polyclonal antibody may be purified by any methods known to those in the art and may be produced from any animal hosts including goats, rabbits, sheep, monkeys, horses, pigs, cattle, dogs, etc. The monoclonal antibody may be produced using any technique that provides the production of antibody molecules through continuous culture of a cell line. Such techniques include, but are not limited to, hybridoma techniques, human B-cell line hybridoma techniques and EBV-hybridoma techniques.

The pharmaceutical composition of the present invention may contain, as active ingredients, a chemical substance, a nucleotide, an antisense, siRNA, oligonucleotide and a natural extract. The pharmaceutical composition or combined formulation of the present invention may be prepared using pharmaceutically suitable and physiologically acceptable adjuvants in addition to the active ingredient. The adjuvants may include an excipient, a disintegrant, a sweetener, a binder, a coating agent, an expander, a lubricant, a glidant, a flavoring agent, a solubilizing agent, etc. For administration, the pharmaceutical composition of the present invention may be preferably formulated using at least one pharmaceutically acceptable carrier in addition to the active ingredient. When the composition is formulated as a liquid solution, it may contain at least one pharmaceutically acceptable carrier selected from among saline solution, sterile water, Ringer solution, buffered saline, injectable albumin solution, dextrose solution, malto-dextrin solution, glycerol, ethanol, and mixtures thereof. If necessary, other conventional additives including an antioxidant, buffer, a bacteriostatic agent, etc. may be added. In addition, a diluent, a dispersing agent, a surfactant, a binder and a lubricant may be further added to prepare injectable formulations such as aqueous solution, suspension or emulsion, etc., a pill, a capsule, a granule or a tablet.

The pharmaceutical composition of the present invention may be formulated in the form of a granule, powder, a coated tablet, a tablet, a capsule, a suppository, syrup, juice, suspension, emulsion, drop, injectable liquid, or sustained-release formulation of an active compound. The pharmaceutical composition of the present invention may be administered according to a conventional method by an intravenous, intraarterial, intraabdominal, intramuscular, intrasternal, transdermal, intranasal, inhalation, topical, rectal, oral, intraocular or intradermal route. The effective amount of the active ingredient of the pharmaceutical composition according to the present invention means an amount required for prevention or treatment of disease. Thus, the effective amount may be determined depending on various factors including the type of disease, the severity of disease, the type and content of an active ingredient and other components contained in the composition, the type of formulation, the patient's age, weight, general health conditions, sex and diet, the time of administration, the route of administration, the secretion rate of the composition, the period of treatment, and a drug that is used concurrently. For an adult, the composition may be administered once or several times a day. When being administered once or several times a day, the dose of administration may be 0.1 ng/kg-10 g/kg for a compound, 0.1 ng/kg-10 g/kg for a polypeptide, a protein or an antibody, and 0.01 ng/kg-10 g/kg for an antisense nucleotide, siRNA, shRNAi or miRNA, but the scope of the present invention is not limited thereto.

The present invention also provides a method for enhancing cancer cell death, which comprises administering a receptor-interacting protein kinase-3 (RIP3) protein expression inducing agent or activator in combination to an anticancer drug to a cancer cell.

Particularly, the method may comprise: treating the cancer cell with the receptor-interacting protein kinase-3 (RIP3) protein expression inducing agent or activator; and administering an anticancer drug to the treated cancer cells.

Preferably, the cancer cells may be a breast cancer cell, a cervical cancer cell, a liver cancer cell or a colorectal cancer cell, and the anticancer drug may be doxorubicin or etoposide, but the scope of the present invention is not limited thereto.

The present invention also provides a method for screening an anticancer adjuvant, comprising: bringing a test substance into contact with a cancer cell; measuring the expression or activity level of RIP3 (receptor-interacting protein kinase-3) protein in the cancer cell brought into contact with the test substance; and selecting a test substance that shows an increase in the expression or activity level of the RIP3 protein compared to a control sample.

Preferably, the expression or activity level of the RIP3 protein may be measured by any one selected from the group consisting of reverse transcription-polymerase chain reaction (RT-PCR), enzyme-linked immunosorbent assay (ELISA), immunohistochemistry, Western blotting and flow cytometry (FACS), but the scope of the present invention is not limited thereto.

Particularly, the anticancer adjuvant may enhance sensitivity to an anticancer drug. More particularly, the anticancer drug may be preferably doxorubicin, etoposide or taxol, but the scope of the present invention is not limited thereto.

The term "test substance", as used with respect to the screening method herein, means an unknown candidate substance that is used in screening in order to examine whether it influences the expression level of a gene or whether it influences the expression or activity of a protein. The sample may include a chemical substance, a nucleotide, antisense-RNA, siRNA (small interference RNA) or a natural extract, but is not limited thereto.

The present invention also provides a method for monitoring anticancer drug sensitivity, comprising: measuring the expression or activity level of RIP3 protein in a cancer cell; measuring the expression or activity level of RIP3 protein in a normal tissue cell; and determining that, if the measured expression or activity level of the RIP3 protein in the cancer cell is lower than the measured expression or activity level of the RIP3 protein in the normal tissue cell, the cancer cell have anticancer drug resistance.

Preferably, the cancer cells may be a breast cancer cell, a cervical cancer cell, a liver cancer cell or a colorectal cancer cell, and the anticancer drug may be doxorubicin, etoposide or taxol, but the scope of the present invention is not limited thereto.

The present invention also provides a method for enhancing anticancer drug sensitivity, comprising: treating a cancer cells with a RIP3 protein expression inducing agent or activator; measuring the expression or activity level of the RIP3 protein in the treated cancer cell; and determining that, if the expression or activity level of the RIP3 protein after the treatment is 50-100% higher than that of a control sample before the treatment, anticancer drug sensitivity is enhanced.

The present invention also provides a biomarker composition for diagnosis of anticancer drug sensitivity, comprising RIP3 gene or a protein expressed from the gene.

As used herein, the term "diagnosis" includes determining the susceptibility of a subject to a certain disease or disorder; determining whether a subject has a certain disease or disorder; determining the prognosis of a subject suffering from a certain disease or disorder; or the rametrics (for example, monitoring the condition of a subject to provide information about therapeutic efficacy).

The present invention also provides a kit for diagnosis of anticancer drug sensitivity, comprising a primer for amplifying RIP3 gene or an antibody or aptamer that binds specifically to a protein expressed from the gene.

As used herein, the term "primer" refers to a nucleic acid sequence having a short free 3'-end hydroxyl group, which is a short nucleic acid sequence that may form a base pair with a complementary template and act as a start point for template strand replication. The primer may initiate DNA synthesis in the presence of a reagent for polymerization (e.g., DNA polymerase or reverse transcriptase) and four nucleoside triphosphates in suitable buffer at a suitable temperature. PCR conditions and the lengths of the sense and antisense primers may be suitably selected according to techniques known in the art.

The kit of the present invention may comprise an antibody binding specifically to a marker component, a secondary antibody conjugate having a label that develops color by reaction with a substrate, a substrate solution to be reacted with the label, a wash buffer, and an enzymatic reaction stop buffer, etc. Further, the kit may be made of a plurality of packagings or compartments including the reagent components used.

The label of the secondary antibody conjugate may be preferably a conventional color development material that develops color. It may be selected from among fluoresceins such as HRP (horseradish peroxidase), alkaline phosphatase, colloid gold, FITC (poly L-lysine-fluorescein isothiocyanate), RITC (rhodamine-B-isothiocyanate), etc., and dyes.

The present invention also provides a method for providing information required for diagnosing prognosis of anticancer drug sensitivity, comprising: measuring the expression level of RIP3 in a cancer patient sample; measuring the expression level of RIP3 in a normal control sample; and determining that, if the measured expression level of the RIP3 protein in the cancer patient sample is lower than the measured expression level of the RIP3 protein in the normal control sample, the cancer patient sample has anticancer drug resistance.

Particularly, the expression level of RIP3 may be measured by an antigen-antibody reaction. More particularly, the antigen-antibody reaction may be performed according to quantitative or qualitative immunoassay protocol known in the art. The immunoassay formats may include, but are not limited to, enzyme-linked immunosorbent assay (ELISA), radioimmunoassay (RIA), sandwich assay, Western blotting, immunoprecipitation, immunohistochemical staining, flow cytometry, fluorescence assisted cell sorting (FACS), enzyme-substrate coloring assay, and antigen-antibody aggregation.

As used herein, the term "patient sample" may be intended to a sample including a tissue, a cell, whole blood, serum, plasma, saliva, phlegm, cerebrospinal fluid and urine, which show a difference in the expression level of RIP3, which is a biomarker for diagnosis of anticancer drug sensitivity, from that in a normal control, but the scope of the present invention is not limited thereto.

Mode For Invention

Hereinafter, the present invention will be described in detail with reference to examples. It is to be understood, however, that these examples are for illustrative purposes only and are not intended to limit the scope of the present invention. The examples of the present invention are provided so that this disclosure will be thorough and complete, and will fully convey the scope of the present invention to those skilled in the art.

EXPERIMENTAL EXAMPLES

The following experimental examples provide experimental examples that are applied commonly to examples of the present invention.

1. Reagents

RIP3 antibody was purchased from Abcam. Actin antibody, doxorubicin, etoposide, 5-AD and 5-AZA were purchased from Sigma-Aldrich.

2. Cell Culture

Various cancer cell lines were cultured in media recommended by the ATCC. DLD1, HeLa and MCF7 were cultured in DMEM media supplemented with 10% fetal bovine serum, 2 mM glutamine, 100 U/mL of penicillin and 100 ug/mL of streptomycin. HCC1937, BT-549, MDA-MB231, MDA-MB468, SK-BR3, ZR75-1 and T47D were cultured in RPMI supplemented with 10% fetal bovine serum, 2 mM glutamine, 100 U/mL of penicillin and 100 ug/mL of streptomycin.

3. Normal Human Cells

Mammary epithelial cells (HMEs) were obtained from Clonetics Corp. (San Diego, Calif.). HMLEs (of a normal mammary epithelial cell were immortalized with hTERT, and also infected by retrovirus with SV40 large and small T antigens.

4. Preparation of Human Breast Cancer Tissue

Human breast cancer and control normal samples were obtained from Yonsei University College of Medicine (Seoul, Korea). In all cases, informed written consent was obtained from all participants, and this study was performed under the approval of the Institutional Review Board (IRB) of Yonsei University.

5. Lentiviral shRNA Experiments

A MISSION short-hairpin RNA (shRNA) plasmid that targets the coding region or 3' UTR of hRIP3 mRNA (NM_006871) or a non-target control sequence (NM-027088) were obtained from Sigma-Aldrich. A Lentivirus plasmid was transfected into 293T cells (System Biosciences, LV900A-1) using Lipofectamine 2000 (Invitrogen, 11668019). Pseudoviral particles were collected at 2 days after transfection of the Lentivirus plasmid and infected into various cancer cells in the presence of polybrene (10 μg/mL). At 2 days after infection, infected cells were selected with puromycin, and RIP3 knockdown was confirmed by immunoblotting. Cells without endogenous RIP3 were afterwards treated with 5-AD for 4 days and analyzed by immunoblotting.

6. Western Blotting (Immunoblotting)

Cells were lysed in M2 buffer. Equal amounts of cell extracts were analyzed by SDS-PAGE and immunoblotting, and blots were visualized by enhanced chemiluminescence (ECL, Amersham).

7. Cytotoxicity Assay

Cell viability was determined using tetrazolium dye colorimetric test (MTT assay) at 570 nm.

8. Immunohistochemistry Assay

Immunohistochemistry was performed using the UltraVision LP Detection System TL-060-HD (Thermo Scientific, Bioanalytica) according to the manufacturer's instructions. Thin paraffin sections (4.5 μm) were deparaffinized in xylene and rehydrated in a graded series of ethanol-aqueous solutions. Antigen retrieval was done by heating the slides for 15 min in a microwave oven in 10 mM citrate buffer (pH 6.0). Endogenous peroxidase activity was blocked by incubation in 3% hydrogen peroxide in TBS for 10 min, and then the sections were incubated overnight at 4° C. in 1:300 dilutions of anti-RIP3 antibody. Chromogen was developed for 5 min with 3,3'-diaminobenzidine (TL-015-HD, Thermo Scientific, Bioanalytica, Greece) solution and counterstained with Meyer's hematoxylin. Immunohistochemical staining was evaluated based on the proportion of stained cells and immunostaining intensity. H-score was obtained by multiplying the proportion of stained cells (%) and staining intensity graded 0 (negative), 1 (weak), 2 (moderate), or 3 (strong). H-score ranged from 0 to 300. Staining was carried out for tumor and normal tissue for each sample for the same time. Staining was interpreted by an experienced pathologist blinded to the clinical data.

9. Statistical Analysis

Data were represented by a mean± S. D. Statistical analysis was performed using ANOVA and an unpaired Student's t-test. A P-value of 0.01 or below was considered statistically significant. Statistical calculations were performed using SPSS software for Windows Version 12.0 (SPSS, Chicago, Ill., USA).

Example 1

Analysis of RIP3 Expression in Breast Cancer Cell Line

A cancer cell line was lysed to isolate proteins which were then subjected to Western blotting using SDS-PAGE. RIP3 expression patterns in breast cancer cell line were analyzed, and as a result, it was shown that RIP3 was not expressed in 60% or more of the cell lines. It was found that RIP3 was silenced in the cancer cell lines by a specific mechanism (FIG. 1).

Example 2

Analysis of RIP3 Expression by Demethylating Agent

After a cancer cell line was seeded to a confluence of 10-20%, and then treated two times with 5-AD for 4 days, RIP3 expression patterns in the cell line was analyzed by a Western blotting technique. It was shown that, when three cancer cell lines (HeLa, MDA-MB231, BT549) that express no RIP3 were treated with a demethylating agent (5-AD, 2 uM), RIP3 expression was induced by 5-AD. This result suggests that RIP3 expression in the cancer cell lines is suppressed by methylation (FIG. 2).

In addition, after a cancer cell line was seeded to a confluence of 10-20%, and then treated two times with 5-AZA for 4 days, RIP3 expression patterns in the cell line was analyzed by a Western blotting technique. It was shown that, when the DLD-1 colorectal cancer cell line that did not expresses RIP3 was treated with various concentrations of 5-AZA, a substance similar to 5AD, RIP3 expression was induced. This result indicates that RIP3 expression in the cancer cell line is suppressed by methylation (FIG. 3).

Example 3

Sensitization of Cancer Cell Death by Combined Treatment with Demethylating Agent and Anticancer Drug A cancer cell line was seeded to a confluence of 10-20%, and then treated two times with 5-AD or 5-AZA for 4 days to induce RIP3 expression. The same number of 5-AD treated HeLa and non-treated HeLa cell lines were seeded, and then treated with the same concentration of an anticancer drug. The effect of the demethylating agent on sensitization to cell death was analyzed.

As a result, it was shown that, when treatment with the anticancer drug was performed after RIP3 expression was induced by 5-AD, RIP3 expressing cancer cell line that treated with 5-AD is sensitized to anticancer drug. This suggests that RIP3 is involved in cancer cell line death by an anticancer drug (FIG. 4).

Furthermore, in addition to the case of 5-AD, it was shown that, when treatment with the anticancer drug was performed after RIP3 expression was induced by 5-AZA, the effect of sensitizing the cancer cell line to cell death was obtained (FIG. 5).

Example 4

Effect of Demethylating Agent on Sensitization of Cancer Cell Line to Cell Death by Inhibition of RIP3 Expression Using a Lenti-virus system, a stable cell that continuously inhibit RIP3 expression in a cervical cancer cell line (HeLa cell line) were made. Unlike a non-target cell line, in the case of a shRIP3 cell line, RIP3 expression in the cell line was inhibited by shRNA, even though the cell line was treated with 5-AD. Thus, the effect of RIP3 on sensitization of the cell line by a combined treatment with the anticancer drug and the demethylating agent could be confirmed. Each of a non-target cell line and a shRIP3 cell line was primarily seeded to a confluence of 10-20%, and then treated two times with 5-AD for 4 days, and whether RIP3 was expressed was examined. In addition, after the same number of cells seeded, the sensitization effect by the combined treatment with the anticancer drug was analyzed using a cell viability assay (MTT assay) (FIG. 6).

Because the demethylating agent (5-AD or 5-AZA) is not a specific drug for a certain protein, it may cause expression of various proteins in addition to RIP3. Thus, in order to determine whether sensitization to cell death by the combined treatment with the anticancer drug and the demethylating agent is an effect induced by proteins other than RIP3, an experiment was performed using the shRIP3 cell line that specifically inhibits RIP3 expression. In the non-target cell line, when the cancer cell line was treated with 5-AD, the combined treatment with the anticancer drug showed the effect of sensitizing the cancer cell death by RIP3 expression, but in the shRIP3 cell line in which RIP3 expression was specifically inhibited, RIP3 was not expressed by the shRNA system, even though the cell line was treated with 5-AD. When a cell viability assay was performed based on such results, it could be seen that, in the case of the shRIP3 cell line that expresses no RIP3, the sensitization effect was inhibited, suggesting that RIP3 is an important molecule in the sensitization of cancer cells death induced by the combined treatment with the demethylating agent and the anticancer drug. In addition, it suggests that promoting RIP3 expression is a novel anticancer strategy that may increase the death of cancer cell.

Example 5

Immunostaining Assay of Normal Breast Tissue and Breast Cancer Tissue

Tumor tissue and non-tumor tissue were isolated from 132 breast cancer patients, and paraffin blocks were prepared.

The prepared paraffin block was sectioned to a thickness of 4.5 μm, and then plated on a slide. The sections were deparaffinized in xylene and rehydrated in a graded series of ethanol-aqueous solutions, and then treated with hydrogen peroxide to eliminate non-specific enzymatic reaction, followed by treatment with citric acid solvent to dissociate latent antigen. Then, it was incubated with diluted normal serum for 20 minutes to block non-specific reaction, and then reacted with RIP3 (1:300) for 24 hours. After washing with water, the incubated material was incubated with biotin-conjugated secondary antibody for 30 minutes, followed by washing with water. After it was incubated with an avidin-biotin complex for 30 minutes, and then washed with water, it was treated with a DAB color development solution for 5 minutes. Next, the nucleus was stained with hematoxylin, washed with water, and then subjected to a mounting process.

The intensity of color development by DAB was graded 0 (no color development), 1 (weak color development), 2 (moderate), or 3 (strong color development), and H-score was obtained by multiplying the proportion of stained cells (%) and staining intensity. Staining was interpreted by an experienced pathologist.

In the experimental results, RIP3 in typical normal breast tissue and breast cancer tissue was imaged, and the results are shown as H-score (FIGS. 7, 8 and 9). It could be seen that the expression level of RIP3 was significantly lower in the cancer tissue than in the normal breast tissue.

Example 6

Viability Assay of RIP3-Silenced HT-29 Cells by Treatment with Various Concentrations of Anticancer Drug HT-29 cells (American Tissue Culture Collection) were cultured in a 37° C. incubator using DMEM medium supplemented with penicillin-streptomycin (10 IU/ml) and 10% FBS. The shRNAi double strand used in the present invention was commercially synthesized by Sigma-Aldrich. The shRNA used in the present invention was designed so as to target the coding region of a human RIPK3 mRNA sequence (NCBI Reference sequence NM_006871).

First, cultured HT-29 cells were dispensed in a 35-mm dish at a density of $2 \times 10^5$ cells. On the next day, the cells were infected with shRNA particles together with polybrene (10 ug/ml) according to the protocol's instruction. As a control, an shRNA that does not target a specific protein was used (NCBI Reference sequence NM_027088).

To measure the amount of RIP3 protein produced in the infected cells, after the infected HT-29 cells were washed with PBS, and then were lysed with lysis buffer to collect the supernatant, protein was isolated using a Western blot kit (BIO-RARD). The isolated protein was incubated with suitable antibodies (anti-β-actin (1:5,000, Sigma), anti-RIP3 (1:1,000, Abcam) and secondary HRP-conjugated antibody (Jackson), and then HRP was detected using an Immunobilon Western Chemiluminescent HRP substrate kit (Thermo).

As a result, as shown in FIG. 10, the RIP3 protein was not substantially detected in the HT-29 cells infected with RIP3 shRNA. This suggests that the infected RIP3 shRNA effectively knocks down the RIP3 gene.

In the present invention, in order to examine whether the RIP3 gene is associated with anticancer drug sensitivity, HT-29 cells infected with RIP3 shRNA were treated with varying concentrations of doxorubicin and etoposide, and then the cell viability of the cancer cells was measured. Particularly, HT-29 cells infected with RIP3 shRNA were treated with 2.5 uM and 5 uM of doxorubicin and 50 uM and 100 uM of etoposide, and then incubated for 48 hours. After the medium was replaced with a fresh medium containing 0.1 mg of MTT (3-([4,5-dimethylthiazol-2-yl]-2,5-diphenyltetrazolium bromide), the cells were further incubated for 2 hours. Colorimetric analysis was performed on a precipitate obtained by reducing a tetrazolium salt, in which viable cells is dissolved, into purple formazan crystal. Next, the medium was removed, and the produced formazan crystal was dissolved in 500 ul of DMSO, and the absorbance was measured using an ELISA reader at 570 nm. Cell viability was expressed as a percentage relative to the control taken as 100% viability.

As a result, as shown in FIG. 10 (right), in the control group, the cell viability decreased dependently on the concentration of doxorubicin and etoposide, whereas in the test group in which RIP3 was knocked down with shRNA, the cell viability increased compared to that of the control group.

Example 7

Viability Assay of RIP3-Silenced T47D Cells by Treatment with Various Concentrations of Anticancer Drug In order to examine whether RIP3 also has an effect on breast cancer cells, RIP3-expressing T47D cells were used. First, the cells were infected with RIP3 in the same manner as described in Example 6.

The results of Western blotting indicated that the RIP3 was not substantially detected in the T47D cells infected with RIP3 shRNA and that the RIP3 gene was effectively knocked down (FIG. 11). In order to examine whether RIP3 increases anticancer drug sensitivity in T47D breast cancer cells, an MTT assay was performed. A control group and a RIP3-knocked down test group were incubated with doxorubicin, etoposide and taxol at the concentrations shown in FIG. 11 (right) for 48 hours. The results of the MTT assay indicated that the cells of the control group were killed dependently on the concentration of the anticancer drugs, whereas the anticancer drug resistance of the RIP3 cell line, particularly the etoposide-treated test group, significantly increased compared to that of the control group.

From the above results, it could be found that the regulation of RIP3 expression influences the anticancer drug resistance of cancer cell lines. Particularly, it could be seen that, when RIP3 expression was inhibited, the cancer cells had resistance to the anticancer drug, and thus the activity of the anticancer drug was inhibited, whereas when RIP3 was expressed, the death of cancer cells increased dependently on the concentration of the anticancer drug.

Example 8

Analysis of 10-Year Metastatic Relapse-Free Survival of Breast Cancer Patients

FIG. 12 is a graph showing the 10-year metastatic relapse-free survival of 1,166 breast cancer patients. The expression level of the RIP3 gene was divided into two (above and below 50%), and the survival rate of the patients was analyzed. As a result, the patients with greater than 50% RIP3 expression showed a statistically significant difference ($p<0.0085$), suggesting that the expression level of RIP3 influences the survival rates of the patients. The results were analyzed using the Breast Cancer Gene-Expression Miner v3.0 software designed by Jezequel et al. (Breast Cancer Research and Treatment 2012; 131:765-75).

Although the present invention has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

The invention claimed is:

1. A method for enhancing chemotherapeutic drug sensitivity of cancer cells in a subject in need of cancer treatment, the method comprising:
    administering to the subject a therapeutically effective amount of an RIP3 protein expression inducing agent or activator as an anticancer adjuvant;
    wherein the anticancer adjuvant enhances chemotherapeutic drug sensitivity in the cancer cell; and
    wherein the RIP3 protein expression inducing agent or activator is a 5-aza-2'-deoxycytidine or a 5-azacytidine.

2. The method of claim 1, wherein the cancer is selected from the group consisting of breast cancer, cervical cancer, liver cancer, and colorectal cancer.

3. The method of claim 1, wherein the chemotherapeutic drug is selected from the group consisting of doxorubicin, etoposide, and taxol.

4. The method of claim 1, wherein the cancer cells have a lower expression or activity level of RIP3 protein compared to normal tissue cells.

* * * * *